United States Patent
Anklam et al.

(10) Patent No.: US 11,078,174 B2
(45) Date of Patent: Aug. 3, 2021

(54) PROCESS FOR MAKING ESTERS OF 2,5-FURANDICARBOXYLIC ACID

(71) Applicant: Archer Daniels Midland Company, Decatur, IL (US)

(72) Inventors: Pam Anklam, Lovington, IL (US); William Chris Hoffman, Decatur, IL (US); Stephen J. Howard, Sherman, IL (US); Alexandra Sanborn, Lincoln, IL (US); Mitchell Schultz, Mt. Zion, IL (US); John G. Soper, Mt. Zion, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 16/622,713

(22) PCT Filed: Jun. 20, 2018

(86) PCT No.: PCT/US2018/038415
§ 371 (c)(1),
(2) Date: Dec. 13, 2019

(87) PCT Pub. No.: WO2018/236948
PCT Pub. Date: Dec. 27, 2018

(65) Prior Publication Data
US 2020/0102280 A1    Apr. 2, 2020

Related U.S. Application Data

(60) Provisional application No. 62/523,540, filed on Jun. 22, 2017.

(51) Int. Cl.
*C07D 307/68*    (2006.01)
*B01D 15/18*    (2006.01)
*B01D 15/36*    (2006.01)

(52) U.S. Cl.
CPC ....... *C07D 307/68* (2013.01); *B01D 15/1821* (2013.01); *B01D 15/364* (2013.01); *B01D 2215/023* (2013.01)

(58) Field of Classification Search
None
See application file for complete search history.

(56) References Cited

U.S. PATENT DOCUMENTS

| | | |
|---|---|---|
| 2015/0315166 A1 | 11/2015 | Stensrud et al. |
| 2017/0015642 A1 | 1/2017 | Sokolovskii et al. |
| 2017/0015643 A1 | 1/2017 | Venkitasubramanian et al. |

FOREIGN PATENT DOCUMENTS

| | | |
|---|---|---|
| WO | 2016166421 | 10/2016 |

OTHER PUBLICATIONS

Search Report and Written Opinion of the International Searching Authority for PCT/US2018/038415 dated Sep. 18 (Year: 2018).*

* cited by examiner

*Primary Examiner* — Zinna Northington Davis
(74) *Attorney, Agent, or Firm* — William B. Miller

(57) ABSTRACT

A process is provided for making esters of FDCA, in which an aqueous feed comprising glucaric acid is first reacted with a high boiling first alcohol in the presence of an acid catalyst and with removing water during the reaction, to form a first product mixture comprising a first ester of FDCA and the high boiling first alcohol, then unreacted high boiling first alcohol is removed from the first product mixture. The first ester of FDCA and the high boiling first alcohol is then transesterified with a lower boiling second alcohol selected from the group consisting of methanol, ethanol, isopropanol and n-propanol, to form a second product mixture comprising a second ester of FDCA with the lower boiling second alcohol, and the second ester of FDCA with the lower boiling second alcohol is recovered.

12 Claims, 1 Drawing Sheet

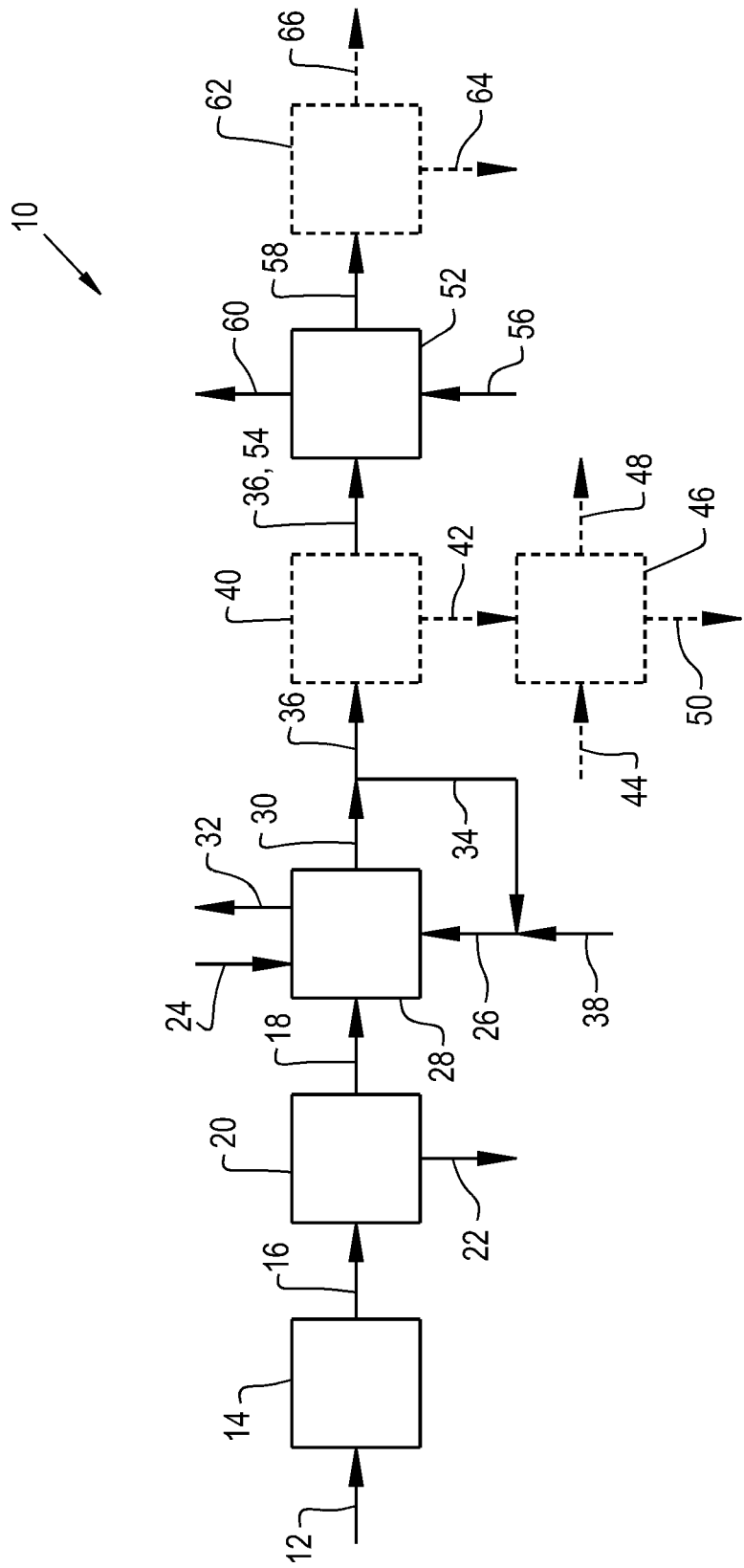

PROCESS FOR MAKING ESTERS OF 2,5-FURANDICARBOXYLIC ACID

This application is a national stage entry of International Application No. PCT/US18/38415, filed Jun. 20, 2018, which itself claims priority to U.S. Provisional Patent Application No. 62/523,540, filed Jun. 22, 2017, the contents of each are incorporated herein by reference.

FIELD OF THE INVENTION

The present invention relates to processes for making the esters of 2,5-furandicarboxylic acid.

BACKGROUND ART

In recent years, an increasing effort has been devoted to identifying new and effective ways to use renewable feedstocks for the production of organic chemicals. The production of furans and furan derivatives from six-carboned carbohydrates has been an area of particular interest, with 2,5-furandicarboxylic acid (or FDCA) being an example as a promising "green" alternative to terephthalic acid.

Although various methods have been proposed for the commercial scale production of FDCA and/or for the production of FDCA esters, most of the work reported to date relies on a chemical dehydration of hexoses, such as glucose or fructose, to the intermediate 5-hydroxymethylfurfural (HMF) or to the ester or ether derivatives of HMF, followed by a Mid-Century-type oxidation to FDCA—and by a subsequent esterification of the diacid, if FDCA esters are the desired product.

One commonly appreciated difficulty with these methods lies in the relative instability of the dehydration intermediates, so that other methods have continued to be evaluated that would proceed through different intermediates and along different pathways.

An example may be found in recently-issued U.S. Pat. No. 9,506,090 to Kambourakis et al., "Method for Synthesizing FDCA and Derivatives Thereof", which describes producing FDCA and derivatives of FDCA from glucose via 3-dehydro-4-deoxy-glucarate (DDG) and derivatives of DDG, at least in part through enzymatic methods. In particular, at column 13, lines 4-15, methods for making diethyl, dibutyl and other esters of FDCA are described in which DDG is first converted to a DDG ester by contacting DDG with methanol, ethanol, propanol, butanol or any C1-C20 alcohol, an inorganic acid such as sulfuric acid and optionally a co-solvent to produce a DDG ester, which can be converted to an FDCA ester by contact with a second inorganic acid. The DDG intermediate from glucose can in turn be prepared by enzymatic means through a variety of pathways and intermediates, see, for example, FIGS. 2A, 2B, 2C, 2D, 2E, 2F, 3B and 3C.

Similar efforts are reported in WO 2016/057628 A1 to Adamian et al. with respect to the manufacture of FDCA, wherein DDG is dehydrated to obtain FDCA by combining DDG with one or more catalysts and/or one or more solvents. In one embodiment, DDG is combined with a solvent and a catalyst in the form of a bromide salt, a hydrobromic acid, an elemental bromine and combinations thereof. In other embodiments, the catalyst is selected from the group consisting of a halide salt, a hydrohalic salt, elemental ion and combinations thereof, while in still other embodiments, the DDG is brought into contact with an acidic solvent in the presence of water or with a carboxylic acid.

A further reference of a similar nature is U.S. Pat. No. 9,260,403 to Yoshikuni et al., wherein (4S,5S)-4,5-dihydroxy-2,6-dioxohexanoic acid (termed DEHU in Yoshikuni) or (4S,5R)-4,5-dihydroxy-2,6-dioxohexanoic acid (DTHU in Yoshikuni) are oxidized to produce (2S,3S)-2,3-dihydroxy-5-oxohexanedioic acid (DOHA in Yoshikuni, and DDG in Adamian or Kambourakis), and then this material is converted to an FDCA ester by dehydrating and cyclizing the DOHA/DDG with a catalyst selected from oxalic acid, levulinic acid, maleic acid, p-toluenesulfonic acid, Nafion® tetrafluoroethylene-perfluoro-3,6-dioxa-4-methyl-7-octenesulfonic acid copolymer, a silica nanocomposite solid acid catalyst, chloroacetic acid, fluoroacetic acid, citric acid, phosphoric acid, sulfuric acid, hydrochloric acid, iodine, hydroiodic acid, an ammonium sulfate salt, a pyridine salt, an aluminum salt, a thorium salt, a zirconium salt, a vanadium salt, a chromium salt, a titanium salt, zinc chloride, aluminum chloride, boron trifluoride, an ion-exchange resin, a zeolite, zirconia, alumina, supported phosphoric acid, activated carbon or a combination of any of these.

Bratulescu, "New Synthesis Method for 2,5-Bis (Alkoxycarbonyl)Furans in One Single Step", *J. Soc. Alger. Chim.*, vol. 10, no. 1, pp. 135-137 (1999) describes the synthesis of diesters of FDCA as useful anaesthetics, bactericidal compounds and materials for the manufacture of reverse osmosis membranes from still another starting material, namely, D-saccharic acid (or equivalently D-glucaric acid, CAS 87-73-0, (2S,3S,4S,5R)-2,3,4,5-tetrahydroxyhexanedioic acid). In Bratulescu's method, D-glucaric acid (hereafter, simply "glucaric acid") is reacted with methanol, ethanol, propanol, isopropanol, butanol, isobutanol or isoamyl alcohol, in the presence of 95% sulfuric acid and by the use of microwave energy, to provide the corresponding diesters of FDCA. Reported yields were 30 percent for the dimethyl esters after 35 minutes' irradiation; 36 percent for the diethyl esters after 35 minutes' irradiation; 40 percent for the dipropyl esters after 40 minutes' irradiation; 31 percent for the diisopropyl esters after 40 minutes' irradiation; 43 percent for the dibutyl esters after 37 minutes' irradiation; 38 percent for the diisobutyl esters after 37 minutes' irradiation; and 42 percent for the diisoamyl esters after 38 minutes' irradiation.

Proceeding through glucaric acid, as in Bratulescu, would seem to offer an advantage over those methods which are reliant on the six-carbon deoxy diacids (Kambourakis et al., Adamian et al. and Yoshikuni et al.) in that methods have been proposed for making glucaric acid by traditional chemical synthesis methods and without the necessity of enzymatic conversions, see, e.g., U.S. Pat. Nos. 9,434,709 and 9,156,766 both to Boussie et al. The method proposed by Bratulescu would further appear to be considerably simpler than the methods outlined in Kambourakis et al., Adamian et al. and Yoshikuni et al., but a common shortcoming of all of these methods is that all involve the use of highly acidic and corrosive reaction conditions. A significant shortcoming of Bratulescu's method, however, is that while FDCA and/or its diesters have been proposed and are being evaluated for production at many thousand tonne, commodity-scale levels that would preferably make use of continuous processing methods, the use of microwaves in such a context involves significant challenges and introduces its own complexities for a manufacturer.

A still more recent proposal to synthesize muconic acid and furan chemicals inclusive of diesters of FDCA from aldaric acids, such as galactaric acid and glucaric acid, is described in US 2017/0137363 to Asikainen et al. Asikainen et al. acknowledge a prior 2008 publication in FR 2723945 wherein aldaric acids were dehydroxylated to such furan chemicals, but indicate these known methods should be avoided as using strong mineral acids and long reaction times, and prescribe instead the use of a combination of a transition metal catalyst, such as a methyl trioxo rhenium catalyst, together with a light alcohol such as methanol as a solvent and hydrogen as a reductant, to produce furoic acid, furoic acid methyl ester, furandicarboxylic acid and furandicarboxylic acid methyl ester from aldaric acids, especially, galactaric acid but also mentioning glucaric acid. Asikainen et al. also describe earlier failed attempts (whether the attempts were made by Asikainen or by others is not stated) to make use of light (i.e., short) alcohols such as methanol, ethanol and n-butanol for the reduction step, and suggest hydrogen is to be preferred as a reductant as being cheaper than "other prior art reductants, such as 1-butanol", as not posing the separation difficulties associated with other reductants than alcohols and as being capable of recycle.

Although no actual working examples are given by Asikainen et al. using glucaric acid as a starting material, examples from galactaric acid and using methanol as the solvent produce a range of materials, namely, 2,4-hexanedioic acid, 2,4-hexanedioic acid 1,6-dimethyl ester, 2-furancarboxylic acid, 2-furancarboxylic acid methyl ester, 2,5-furandicarboxylic acid and 2,5-furandicarboxylic acid 2,5-dimethyl ester, and selectivity to and yields of FDCA and its dimethyl ester are low in comparison to other products across a range of temperature conditions and residence times. A subsequent example using ethanol as the solvent results in the production of 2,4-hexanedioic acid 1,6-diethyl ester, with no mention of furanic species at all, while a further example with 1-butanol yields the 1,6-dibutyl ester of 2,4-hexanedioic acid and again mentions nothing of furanic species being found in the product.

Moreover, there are other practical concerns with Asikainen et al's proposed process, for example, carrying out the process under a hydrogen atmosphere poses significant safety concerns and recycling hydrogen as Asikainen et al. propose is far from the simple, economical task that Asikainen et al. would seem to suggest, so that, in sum, while it is evident that a route to the light/short chain diesters of FDCA starting from other materials generally than the furanic dehydration products—HMF, ethers and esters of HMF—has been seen as highly desirable, and in particular a process starting from an aldaric acid such as glucaric acid has been appreciated as highly needed, nevertheless there is still substantial room for improvement on the methods that have been proposed to date from alternative starting materials to the furanic dehydration products.

SUMMARY OF THE INVENTION

The following presents a simplified summary of the invention in order to provide a basic understanding of some of its aspects. This summary is not an extensive overview of the invention, thus the mention or omission of a particular feature should not be understood as implying, respectively, that the feature is indispensable or of lesser significance. The sole purpose of this summary is to present some concepts of the invention in a simplified form as a prelude to the more detailed description that is presented later.

With this understanding, the present invention in one aspect relates to a process for making the esters of 2,5-furandicarboxylic acid, and particularly the dimethyl, diethyl or dipropyl esters of FDCA for use as monomers in the production of polyesters and other types of polymers with biobased content, comprising:

reacting an aqueous feed comprising glucaric acid with a high boiling first alcohol in the presence of an acid catalyst and with removing water during the reaction, to form a first product mixture comprising a first ester of FDCA and the high boiling first alcohol;

removing unreacted high boiling first alcohol from the first product mixture;

combining the first ester of FDCA and the high boiling first alcohol with a lower boiling second alcohol selected from the group consisting of methanol, ethanol, isopropanol and n-propanol;

transesterifying the first ester with the lower boiling second alcohol to form a second product mixture comprising a second ester of FDCA with the lower boiling second alcohol; and recovering the second ester of FDCA with the lower boiling second alcohol.

From another, broader perspective, the present invention can be seen as relating to a process for making esters of FDCA from dextrose, in which dextrose is oxidized to provide a mixture of materials including gluconic acid as well as glucaric acid, a glucaric acid-enriched fraction is chromatographically isolated from the mixture using an amphoteric ion exchange resin, and then glucaric acid from that glucaric acid-enriched fraction is used to form one or more esters of FDCA.

BRIEF DESCRIPTION OF THE DRAWINGS

FIG. 1 is a schematic drawing of an embodiment of a process of the present invention.

DETAILED DESCRIPTION OF EMBODIMENTS

As used in this application, the singular forms "a", "an" and "the" include plural references unless the context clearly indicates otherwise. The term "comprising" and its derivatives, as used herein, are similarly intended to be open ended terms that specify the presence of the stated features, elements, components, groups, integers, and/or steps, but do not exclude the presence of other unstated features, elements, components, groups, integers and/or steps. This understanding also applies to words having similar meanings, such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers, and/or steps. The term "consisting essentially of", as used herein, is intended to specify the presence of the stated features, elements, components, groups, integers, and/or steps, as well as those that do not materially affect the basic and novel characteristic(s) of stated features, elements, components, groups, integers, and/or steps. Terms of degree such as "substantially", "about" and "approximately" as used herein mean, regardless of the degree of precision conventionally understood by the number of significant figures used in numerically describing a particular attribute, plus or minus five (5) percent from a stated value.

Where specific numerical values are used to quantify certain parameters relating to the invention without an accompanying term of degree, and where the specific numerical values are not expressly part of a numerical range, it will be understood that each such specific numerical value provided herein is to be construed as providing literal support for a broad, intermediate and narrow range of values for the parameter in question. The broad range shall be the numerical value plus and minus 60 percent of the numerical value, rounded to two significant digits. The intermediate range shall be the numerical value plus and minus 30 percent of the numerical value, rounded to two significant digits, while the narrow range shall be the numerical value plus and minus 15 percent of the numerical value again to two significant digits. Further, these broad, intermediate and narrow numerical ranges should be applied not only to the specific values, but also to the differences between these specific values. Thus, if the specification describes a first pressure of 110 psia for a first stream and a second pressure of 48 psia (a difference of 62 psia) for a second stream, the broad, intermediate and narrow ranges for the pressure difference between these two streams would be 25 to 99 psia, 43 to 81 psia, and 53 to 71 psia, respectively.

Where the present description uses numerical ranges to quantify certain parameters relating to the invention, it will be similarly understood that these ranges are to be construed as providing literal support for claim limitations that only recite the lower value of the range as well as claim limitations that only recite the upper value of the range.

Unless otherwise indicated, any definitions or embodiments described in this or in other sections are intended to be applicable to all embodiments and aspects of the subjects herein described for which they would be suitable according to the understanding of a person of ordinary skill in the art.

As indicated above, the present invention in one aspect relates to a process for making esters of FDCA, characterized by and including the steps of reacting an aqueous feed comprising glucaric acid with a high boiling first alcohol in the presence of an acid catalyst and with removing water during the reaction, to form a first product mixture comprising a first ester of FDCA and the high boiling first alcohol; removing unreacted high boiling first alcohol from the first product mixture; combining the first ester of FDCA and the high boiling first alcohol with a lower boiling second alcohol selected from the group consisting of methanol, ethanol, isopropanol and n-propanol; transesterifying the first diester with the lower boiling second alcohol to form a second product mixture comprising a second ester of FDCA with the lower boiling second alcohol; and recovering the second ester of FDCA with the lower boiling second alcohol. The diesters of FDCA with the lower boiling second alcohol have particular utility, as already mentioned, as monomers in the production of polyesters and other types of polymers with biobased content.

A "high boiling first alcohol" as used herein refers to any alcohol with a boiling point of at least 120 degrees Celsius, though preferred alcohols will be those which meet these qualifications and find widespread use as plasticizer alcohols, for example, the $C_4$ to $C_{11}$ linear alcohols and $C_4$ to $C_{11}$ branched alcohols, especially, but not being limited to, 2-ethyl-1-hexyl alcohol, isobutyl alcohol, 2-propylheptyl alcohol, isononyl alcohol, isodecyl alcohol, isooctyl alcohol, isoamyl alcohol, isohexyl alcohol, fusel oil and mixtures of any of these.

By employing a particular plasticizer alcohol and making diesters of FDCA with the plasticizer alcohol, a portion thereof can be recovered for sale as a plasticizer or for other productive uses, as the market's requirements for the second ester as a monomer or for the first ester for such alternative uses may change over time, while the remainder is used to make particularly the dimethyl, diethyl, diisopropyl or dipropyl esters of FDCA for monomeric applications.

For example, based on the greater utility of phthalates as compared to terephthalates as plasticizers for PVC, we expect that the 2,3-diester of FDCA with a selected plasticizer alcohol will likely be of higher value as a plasticizer for PVC as compared to the 2,5-diester, so that it may be desirable from time to time to recover a separate plasticizer product fraction enriched in the 2,3-diester of FDCA with the selected plasticizer alcohol, following an optional step to separate and recover such an enriched fraction from the first product mixture, e.g., by precipitation and filtration, distillation or chromatography.

As well, those skilled in the art will appreciate that a 2,3-diester of FDCA may be converted to an anhydride in the same manner as phthalate anhydrides are presently made, and used in unsaturated polyester resins as a still further alternative, productive use of a portion of the first diester of FDCA with a high boiling first alcohol, with again the remainder being used as a feedstock for the production of a dimethyl, diethyl, diisopropyl or dipropyl ester of FDCA for use as a monomer in the production of polyester polymers.

The two step/two reaction sequence of the present invention thus can provide a complementary second product in a related but distinct market segment, that can comprise a lesser or greater proportion of the saleable products from the process as a whole according to market demands and provide an opportunity to improve the economics of the overall process.

More generally, the present invention can be seen as providing an efficient method for the production from glucaric acid of esters of a high boiling first alcohol and of esters of a lower boiling second alcohol with FDCA, where the esters of a high boiling first alcohol on the one hand and the esters of a lower boiling second alcohol on the other hand—or derivative materials which those of skill in the art will recognize may be made from these esters, for example, the anhydrides just mentioned or oligomers or polymers formed by transesterification of a diester of FDCA such as formed, for example, with the high boiling first alcohol with a polyol such as ethylene glycol or 1,3-propanediol—may serve different needs and solve different problems.

By employing the two reaction sequence of the present invention, and particularly by the selection of a high boiling first alcohol which is immiscible with water, a biphasic system can be established whereby the first esters are retained in an organic phase comprised of excess high boiling first alcohol, and water generated in the cyclization and dehydration of glucaric acid to FDCA and by the esterification of the FDCA to form the first esters may be removed to shift the equilibrium in favor of the desired first ester product. Preferably, the reaction is carried out with continuous removal of the water. In an alternative embodiment, where a high boiling first alcohol is selected which is miscible with water, water generated in the cyclization and dehydration of glucaric acid to FDCA and by the esterification of the FDCA to form the first esters may be removed by the use of a hygroscopic material or adsorbent to help drive the esterification reaction forward.

High yields can in this manner be achieved of the first esters. The conventional transesterification of the first esters to the desired dimethyl, diethyl, diisopropyl or dipropyl esters of FDCA can be done virtually quantitatively, with yields from the first esters to the second preferably of at least 70 percent, more preferably at least 80 percent and still more preferably at least 90 percent, so that commercially viable yields can be achieved of the second, light/short chain diesters without the shortcomings of the prior methods.

The practice of biphasic synthesis and the esterification art are sufficiently well developed that those skilled in the art will be well able to carry out the process of the present invention in either the biphasic or alternative embodiments based on the above summary, but the benefits and advantages of the present invention will be more fully understood by reference to the accompanying figure, in which a process of the present invention is schematically illustrated in reference to one particular, preferred embodiment. Those skilled in the art will appreciate that this particular, preferred embodiment (and variations thereof detailed below) is illustrative only, and accordingly should not be taken as limiting the present invention, as defined in the claims that follow.

Turning now to FIG. 1, an embodiment 10 is depicted in which a supply of dextrose 12 is first oxidized in an oxidation step 14 to generate a mixed acids product 16 including D-glucaric acid, from which an aqueous, glucaric acid-containing feed 18 is generated following a separation step 20 to separate other acids 22 in the mixed acid product 16 away from the desired glucaric acid for aqueous feed 18.

D-glucaric acid is commercially available and produced by the nonselective chemical oxidation of glucose, using nitric acid as the oxidant, though other methods have been proposed for producing glucaric acid for the aqueous feed 18 and would be preferred.

As related in U.S. Pat. No. 8,669,397 to Boussie et al., U.S. Pat. No. 2,472,168 illustrates a method for the preparation of glucaric acid from glucose using a platinum catalyst in the presence of oxygen and a base. Further similar examples of the preparation of glucaric acid using a platinum catalyst in the presence of oxygen and a base may be found in the *Journal of Catalysis*, vol. 67, pp. 1-13 and 14-20 (1981). Other prior oxidation methods referenced by Boussie et al. include those described in U.S. Pat. No. 6,049,004 (use of solvent extraction with dialkyl ether to crystallize glucaric acid following nitric acid oxidation, and avoid necessity of neutralization); U.S. Pat. No. 5,599,977 (nitric acid oxidation with gas injection into reaction product for moderating temperature increases, followed by neutralization); U.S. Pat. No. 6,498,269 (use of an oxoammonium catalyst/halide co-catalyst system); *J. Chem. Technol. Biotechnol.*, vol. 76, pp. 186-190 (2001) (D-glucaric acid by oxidation of molasses in packed beds using vanadium pentoxide catalyst with nitric acid in oxidizing medium); *J. Agr. Food Chem.*, vol. 1, pp. 779-783 (1953); *J. Carbohydrate Chem.*, vol. 21, pp. 65-77 (2002) (4-AcNH-TEMPO-catalyzed oxidation of D-glucose to D-glucaric acid using elemental chlorine or bromine as the terminal oxidant); *Carbohydrate Res.*, vol. 337, pp. 1059-1063 (2002) (TEMPO-mediated oxidation of glucose to glucaric acid using bleach). However, these processes are characterized by Boussie et al. as suffering from various economic shortcomings resulting from, among other issues, process yield limitations and the requirement for additional reaction constituents.

Against the background of these prior published oxidation methods, U.S. Pat. No. 8,669,397 to Boussie et al. describes a catalytic method for producing glucaric acid from glucose, with the glucaric acid then being converted by hydrodeoxygenation to adipic acid. According to Boussie et al., glucose can be converted to glucaric acid in high yield by reacting glucose with oxygen (in the form of air, oxygen-enriched air or oxygen with other constituents substantially inert to the reaction) in the presence of a catalyst typically including one or more of palladium and platinum optionally in the presence of one or more other d-block metals (e.g., Rh or Ru), alone or in combination with one or more rare earth metals, alone or in combination with one or more main group metals (e.g., Al, Ga, Tl, In, Sn, Pb or Bi) on a support or unsupported, but in the absence of added base.

Processes for separating the glucaric acid from other components of the reaction product from Boussie et al's oxidation process are described in US 2016/0090346 to Diamond et al. The processes described in Diamond et al. are summarized as involving contacting a separation media in a separation zone with the reaction product of Boussie et al., separating at least a portion of the glucaric acid or a salt thereof in the reaction product from other, on-path intermediates to the glucaric acid (especially gluconic acid, which is formed at comparable levels to glucaric acid in Boussie et al's process) which intermediates are contained in a raffinate, removing the raffinate from the separation zone, and eluting the glucaric acid or its salt from the separation media with an eluent comprising water. A preferred separation media is described as comprising a weakly basic anion exchange chromatography resin employed in a simulated moving bed, especially a glucarate form of an anion exchange chromatography resin. Combinations of these resins with weak base and strong base functionalities are also described as useful. A particular example of a process for the separation of glucaric acid from gluconic acid and other on-path intermediates is given in Example 2, and involved a simulated moving bed system employing a Lanxess Lewatit MDS 4368 styrene/divinylbenzene cross-linked macroporous anion exchange resin (characterized as having 75-80% weak base and 25-20% strong base functionality) with 1.4 eq/L exchange capacity and 0.3 mm bead size. The free-base and hydroxyl forms of the resin were converted to the glucarate form by exposure to a 1M glucaric acid solution before use. Enrichment of the glucaric acid content was said to be enabled from 47.9 mol percent in the feed to 90.1 mol percent in the extract, with 97 percent by mass of unconverted glucose and on-path intermediates being concentrated in the raffinate and available for recycle back to the oxidation process of Boussie et al. to make additional glucaric acid.

For purposes of the present invention, the method described in Boussie et al. is preferred to the other oxidation methods just described for preparing the glucaric acid for the aqueous feed 18, though we would propose an alternative method 20 to that of Diamond et al. for separating the glucaric and gluconic acids in a mixture 16 of these acids.

Our improved separation step 20 would involve chromatographic separation by means of an amphoteric resin rather than a weakly basic anion exchange resin, preferably in a simulated moving bed system. Examples are given below for demonstrating the surprising effectiveness of such resins for separating these carboxylic acids of generally very similar properties. In this regard, amphoteric resins contain both weakly acidic positive and strongly basic negative functional groups attached to a polystyrene matrix and are typically thought of as useful only for the separation of an electrolyte and non-electrolyte or for the separation of two different electrolytes (e.g., sugar/salt, glycerin/salt, caustic material/salt, salt/salt).

A preferred method for separating glucaric acid from gluconic acid in a mixture such as produced by Boussie et al. according to our conception would however involve providing a glucaric acid-containing mixture having at least 35% (e.g., from 40%-55%) concentration of the glucaric acid; running an extraction of the mixture through a chromatographic column configured with an amphoteric resin, such that the desired glucaric acid feed material elutes preferentially from the mixture. We have surprisingly found that an amphoteric resin provided a preferential affinity ratio of at least 2:1 to 3:1 for glucarate:gluconate, indicating superior separation potential to the weakly basic anion exchange resins taught by Diamond et al., with improved performance of the amphoteric resin over time as well compared to a weakly basic anion exchange resin.

The glucaric acid recovered from the mixture in the method described in Diamond et al, or according to the improved method just described, would then be used to make up the aqueous feed 18, while the gluconic acid could be diverted with minor amounts of other acids found in the mixed acids product 16 from oxidation step 14 to other, known productive uses, for example, as a food additive or in cleaning products or for forming gluconate salts for medical applications.

Biological routes to glucaric acid have also been proposed and could be used to provide the glucaric acid for aqueous feed 18, see, for example, T. S. Moon et al., "Production of Glucaric Acid from a Synthetic Pathway in Recombinant *Escherichia coli*", Appl. Environ. Microbiol., vol. 75, no. 3, pp. 589-595 (February 2009), see also WO 2009/145838 to Moon et al., describing the conversion of glucose to glucaric acid using a engineered *Escherichia coli* expressing myo-inositol-1-phosphate synthase and myo-inositol oxygenase. The yield of glucaric acid from this construct is ~2.5 g/L. These yields though promising make it impractical for industrial production of glucaric acid.

An alternative biological pathway is proposed in US 2015/0152448 to Ito et al., wherein a method is described for oxidizing glucose to glucaric acid using *Pseudogluconobacter* as catalyst.

Still another biological route to glucaric acid, in the form of a glucarate salt that will provide glucaric acid in aqueous solution, is proposed in U.S. Pat. No. 9,528,133 to Kambourakis et al., wherein several enzymatic transformations are described from glucose via a strain expressing alditol dehydrogenase and uronate dehydrogenase.

Further, since in aqueous solution glucaric acid exists in equilibrium with two monolactones, D-glucaro-1,4-lactone and D-glucaro-6,3-lactone, and with the dilactone D-glucaro-1,4:6,3-dilactone, see Brown et al., "An NMR Study of the Equilibration of D-Gluconic Acid with Lactone Forms in Aqueous Acid Solutions", Journal of Carbohydrate Chemistry, vol. 26, pp. 455-467 (2007), the aqueous feed 18 can be in the form of an aqueous solution of the commercially-available dilactone or obtained or derived from a method for the synthesis of the dilactone, see, for example, Gehret et al., "Convenient Large-Scale Synthesis of D-Glucaro-1,4:6,3-dilactone", J. Org. Chem., vol. 74, pp. 8373-8376 (2009).

Consequently, it will be understood that an "aqueous feed comprising glucaric acid" as used herein includes an aqueous feed comprising one or more of glucarodilactones, saccharic acid salts, and the monolactones and dilactones of glucaric acid and any combination of these materials, together with any other terms by which any of these compounds have been known in the art.

Preferably, however the glucaric acid for aqueous feed 18 is obtained, by biological or non-biological methods, the aqueous feed 18 will consist essentially of glucaric acid or a mixture of glucaric acid and its lactone forms in water, with water being from 1 to 50 percent by weight of the feed 18, preferably being from 10 to 40 percent by weight of the feed 18.

The aqueous feed 18 is then in the illustrated embodiment combined with an acid catalyst 24 and a high boiling first alcohol 26, and undergoes an oxidative esterification step 28 to form a first product mixture 30 comprising a first diester of FDCA and the high boiling first alcohol. As earlier related, by the selection of a high boiling first alcohol which is immiscible with water, a biphasic system can be established whereby the first diesters are retained in an organic phase comprised of excess high boiling first alcohol, and water generated in the cyclization and dehydration of glucaric acid to FDCA and by the esterification of the FDCA to form the first diester may be removed, as indicated schematically in FIG. 1 by the arrow 32, to shift the equilibrium in favor of the desired first diester product. Preferably, the reaction is carried out with continuous removal of the water and under mild conditions for avoiding degrading the first diester of FDCA. Subsequently, excess unreacted high boiling first alcohol is recovered for recycle and reuse in the oxidative esterification step as high boiling first alcohol recycle stream 34, with the remainder after removal of unreacted high boiling first alcohol forming a transesterification feed 36 of the first diester of FDCA with the high boiling first alcohol. Makeup high boiling first alcohol (38) is added to the recovered and recycled unreacted alcohol (34) as needed.

The acid catalyst 24 in the particular embodiment of FIG. 1 can be any homogeneous or heterogeneous acid catalyst for the cyclization and dehydration of glucaric acid to a furandicarboxylic acid, for example, but without limitation thereto, hydrobromic acid (HBr), hydroiodic acid (HI), hydrochloric acid (HCl), nitric acid ($HNO_3$), sulfuric acid ($H_2SO_4$), tosylic acid (p-TSA), phosphoric acid, acetic acid, methanesulfonic acid, trifluorosulfonic acid or heteropoly acid, the known tin (II) esterification catalysts or the homogeneous organotin catalysts of commonly assigned, copending International Application No. PCT/US2017/032233 for "Organotin Catalysts In Esterification Processes Of Furan-2,5-Dicarboxylic Acid (FDCA)".

In one embodiment, a strong mineral acid such as sulfuric acid is simply used for acid catalyst 24. The concentration of the acid may be between 0.1 percent by weight and 20 percent by weight, preferably being between 5 percent by weight and 15 percent by weight, with a temperature for the first esterification reaction being from 100 degrees Celsius to 240 degrees Celsius and the process being carried out over the course of from 1 hour to 24 hours. Preferably, the reaction in this first step 28 is carried out under an inert gas blanket, for example, under a nitrogen blanket, and at temperatures of 220 degrees Celsius or less, more preferably 180 degrees Celsius or less and still more preferably 160 degrees Celsius or less.

Optionally, the transesterification feed 36 is then subjected to a refining step 40 to separate out and recover at least a portion 42 of either the 2,3- or 2,5-diesters of FDCA with the high boiling first alcohol for an alternative use or uses such as have been previously described, for example, for use as a plasticizer for PVC (typically the 2,3-diesters will be favored for this use as compared to the 2,5-diesters), to be made into an anhydride for use in making unsaturated polyester resins and/or as illustrated schematically in FIG. 1, for being combined with a source 44 of a polyol such as ethylene glycol or 1,3-propanediol and reacted in an optional further step 46 for forming an oligomer or polymer product 48 and in the process generating a supply 50 of high boiling first alcohol which can be recycled for use in the esterification step 28. The separation of at least a portion 42 of either of the 2,3- or 2,5-diesters of FDCA with the high boiling first alcohol can be accomplished by any suitable means for differentiating between the 2,3- and 2,5-diesters with the high boiling first alcohol, for example, by distillation, chromatography or solid-liquid extraction.

Where it is desired, as previously described, to provide for the recovery of at least a portion 42 of either the 2,3- or 2,5-diesters of FDCA with the high boiling first alcohol for an alternative use or uses by means of a refining step 40, we have found that by selecting particular acid catalysts 24 for use in the oxidative esterification step 28, the relative proportions of the 2,3- and 2,5-diesters that are produced can be affected. Thus, for example, where it is desired to produce more of the 2,3-diester as a co-product for plasticizer applications, rather than of the 2,5-diester of the lower boiling alcohol for monomeric applications, selection of a triflate catalyst 24, for example, a gallium or hafnium triflate catalyst, or of an acidic carbon catalyst 24 to a lesser degree, will result in a greater proportion of the 2,3-diester of the high boiling first alcohol as compared to the 2,5-diester.

In one embodiment wherein one wishes to provide the opportunity to produce more of the 2,3-diester in this fashion, this could be accomplished by campaigning a single reactor for the oxidative esterification step 28 with different catalysts 24. In another embodiment, reactors could be arrayed in parallel containing different catalysts 24, while in still another embodiment, different catalysts 24 could be employed in different tubes of a multitubular reactor with the use of associated valving and/or manifolds for altering the numbers of tubes in use containing the respective catalysts 24.

In the absence of the optional refining step 40, then the transesterification feed 36 is supplied directly to a transesterification step 52, or if the optional refining step 40 is included, then a remainder 54 of the transesterification feed 36 is supplied after the portion 42 has been recovered for an alternative use or uses as just described.

In the transesterification step 52, diesters of FDCA formed with the high boiling first alcohol in the oxidative esterification step 28 and contained in the transesterification feed 36 or in a remainder 54 of the feed 36 are transesterified in a manner as generally known in the art, in the presence of a suitable catalyst and with a supply 56 of a lower boiling second alcohol selected from the group consisting of methanol, ethanol, isopropanol and n-propanol, to provide a product 58 comprised of the corresponding diesters of FDCA with the second alcohol and with a second recycle 60 of high boiling first alcohol being also produced. Conditions in the transesterification step 52 will preferably again be comparatively mild, at temperatures preferably less than 80 degrees Celsius and more preferably less than 60 degrees Celsius.

In the absence of the optional refining step 40, the product 58 will contain both 2,3- and 2,5-diesters of FDCA with the lower boiling second alcohol, and these may be separated in an optional further refining step 62 into a 2,3-diester enriched product 64 and a 2,5-diester enriched product 66. Of these, the 2,5-diester enriched product 66 will be favored for use as a monomer feed to a separate polymerization process (not shown) for making especially a polyester polymer product.

The present invention is more particularly illustrated by the following, non-limiting examples:

EXAMPLE 1

Glucarodilactones (glucaro-1,4:3,6-dilactone, 28.99 grams, from Chemica Inc., Los Angeles, Calif.), 1-pentanol (300 mL, Sigma-Aldrich, St. Louis, Mo.) and concentrated sulfuric acid (3 mL) were placed in a 3-neck round bottom flask equipped with magnetic stirring, a Dean-Stark trap and condenser. The mixture was heated under argon to reflux and maintained at reflux for 4.5 hours, with continuous removal of water via the Dean-Stark trap. The contents of the flask were then cooled and rinsed with saturated sodium bicarbonate. The organic phase was then collected and rotovapped to remove unreacted 1-pentanol, and to the remainder (57.85 grams, containing both of the 2,3-dipentyl and 2,5-dipentyl furandicarboxylate esters as verified by NMR, as well as the monopentyl esters of FDCA, FDCA and some 2-methyl-5-pentyl furoate) were added twelve (12.0) grams of a solution of 30% sodium methoxide in methanol and an additional 210 mL of anhydrous methanol, for carrying out the second, transesterification step. This mixture was heated to 60 degrees Celsius for 1 hour. The resultant transesterification product mixture was neutralized with citric acid in methanol, and methanol was removed by rotary evaporation. The solids that were left behind were washed with water, yielding a 2,5-FDME solid product at more than 95 percent purity and a 2,3-FDME product in the liquid phase, as determined by $^1$H nuclear magnetic resonance spectroscopy and liquid chromatographic analytical methods. The ratio of 2,5-FUME to 2,3-FUME was about 2:1.

EXAMPLE 2

Glucarodilactones as employed in Example 1 (10.95 grams), 2-ethyl-1-hexanol (110 grams, Sigma-Aldrich, St. Louis Mo.) and concentrated sulfuric acid (1.10 mL) were placed in a 3-neck round bottom flask equipped with magnetic stirring, a Dean-Stark trap and condenser. The mixture was heated under argon to reflux, and maintained at reflux for 2.5 hours with continuous removal of water via the Dean-Stark trap. $^1$H NMR showed the formation of predominantly bis(2-ethyl-1-hexyl) furan-2,3-dicarboxylate and the bis(2-ethyl-1-hexyl) furan-2,5-dicarboxylate. The contents of the flask were cooled and rinsed with saturated sodium bicarbonate. The organic phase was collected, and excess 2-ethyl-1-hexanol removed therefrom by short path distillation. Methanol (77 g) and a solution of sodium methoxide in methanol (3.24 g) were added and the reaction allowed to reflux for 1 hour. TLC analysis indicated the formation of 2,3-FUME and 2,5-FDME. The mixture was cooled and neutralized with a solution of citric acid (5 g) in methanol (10 mL). The resultant solids were washed with hexane and freeze dried to produce 5.76 g of solid product. $^1$H nuclear magnetic resonance spectroscopy indicated a composition of about 84% 2,5-FDME and 16% 2,3-FUME, at molar yields of 42% 2,5-FDME and 8% 2,3-FDME from glucarodilactones.

EXAMPLE 3

Glucarodilactones as employed in Example 1 (49.1 grams), 2-ethyl-1-hexanol (499.96 grams, Sigma-Aldrich, St. Louis Mo.) and concentrated sulfuric acid (2.45 mL) were placed in a 3-neck round bottom flask equipped with magnetic stirring, a Dean-Stark trap and condenser. The mixture was heated under argon to reflux, and maintained at reflux for 4.5 hours with continuous removal of water via the Dean-Stark trap. The contents of the flask were cooled and rinsed with saturated sodium bicarbonate. The organic phase was collected, and excess 2-ethyl-1-hexanol removed therefrom by short path distillation. A solids product was collected after washing with isopropanol and filtering. The collected solids were determined to be predominantly bis (2-ethyl-1-hexyl) furan-2,3-dicarboxylate while the bis(2-ethyl-1-hexyl) furan-2,5-dicarboxylate remained in the liquid phase, as determined by $^1$H nuclear magnetic resonance spectroscopy and liquid chromatographic analytical methods. The liquid fraction containing the bis(2-ethyl-1-hexyl) furan-2,5-dicarboxylate was then placed in 350 mL of anhydrous methanol, and 6.3 grams of a 30% solution of sodium methoxide in methanol were then added. After heating to 60 degrees Celsius and maintaining the temperature for an hour, 2,5-FDME was isolated as a solid by precipitation (17 grams, with a purity in excess of 95 percent by $^1$H nuclear magnetic resonance spectroscopy).

EXAMPLE 4

Glucarodilactones as employed in Example 1 (35 grams), 1-pentanol (499.96 grams, Sigma-Aldrich, St. Louis Mo.) and concentrated sulfuric acid (3.5 mL) were placed in a 3-neck round bottom flask equipped with magnetic stirring, a Dean-Stark trap and condenser. The mixture was heated under argon to reflux, and maintained at reflux for 9 hours with continuous removal of water via the Dean-Stark trap. The contents of the flask were cooled and the organic phase was collected, and excess 1-pentanol removed therefrom by rotary evaporation. HPLC and $^1$H NMR analysis indicated a ratio of 1:2 ratio of 2,3-dipentyl and 2,5-dipentyl furandicarboxylate esters in the crude product mixture. A portion of the mixture was washed with saturated sodium bicarbonate, and the aqueous phase was extracted with hexane and dried over magnesium sulfate. The hexane wash was cooled and solids precipitated from the solution. $^1$H NMR indicated a solids composition of about 75% 2,3-dipentyl furandicarboxylate ester and 24% 2,5-dipentyl furandicarboxylate ester. The filtrate contained predominantly 2,5-dipentyl furandicarboxylate ester at about 80% purity, and the remainder was comprised of the 2,3-dipentylfurandicarboxylate ester. A portion of the crude product mixture (24.55 g) was placed in methanol (123 g) with 4.37 g of a 30% sodium methoxide in methanol solution, and this mixture was heated at reflux for 5 hours. The mixture was then cooled and a sample of solids formed was taken and rinsed with water. The solids were dried and analyzed by $^1$H NMR and showed 2,5-FDME in excess of 95% purity.

EXAMPLE 5

Glucarodilactones as employed in Example 1 (24 grams), 1-pentanol (240 mL, Sigma-Aldrich, St. Louis Mo.) and p-toluenesulfonic acid (7.83 g) were placed in a 3-neck round bottom flask equipped with magnetic stirring, a Dean-Stark trap and condenser. The mixture was heated under argon to reflux, and maintained at reflux with continuous removal of water via the Dean-Stark trap. After sampling at 3 hours, $^1$H NMR analysis indicated the formation of the dipentyl esters. The reaction was allowed to reflux for 13 hours and the reaction was cooled. GC analysis of the product solution indicated a ratio of about 70:30 of 2,5-dipentyl furandicarboxylate ester to 2,3-dipentyl furandicarboxylate ester (the 2,3-diester being produced at about 3.83%), with monoesters also being indicated.

EXAMPLE 6

For demonstrating the manner in which a glucaric acid feed could be generated from a product as produced by Boussie et al., a series of pulse tests were run using an aqueous feed mixture containing 6.3% by weight of gluconate salts, 8.2% by weight of glucarate salts, 0.013% of chloride, 0.025% of sulfur, and 2.7% of other organic acids. 280 mL of the particular Lanxess Lewatit MDS 4368 styrene/divinylbenzene cross-linked macroporous anion exchange resin exemplified in Diamond et al. was loaded for comparison into 2 jacketed glass columns (25 mm×600 mm) and the air bubbles were removed. Both columns were connected to a water bath and heated to 50 degrees Celsius. The columns were rinsed with approximately 10 bed volumes of deionized water, then a first column (column #1) was conditioned with 7 bed volumes of the aqueous feed mixture while a second column (column #2) was conditioned with 7 bed volumes of a prepared saccharic acid solution which had been passed through 400 ml of Dowex 88 sodium form, macroporous strong acid cation exchange resin. Both columns were run upflow during the pretreatment due to swelling of the resin (about 40 percent swelling was observed). After pretreatment, the columns were then rinsed with 10 bed volumes of deionized water.

After the columns were conditioned in this manner, the columns were configured for down flow operation. The valve on top of the column was opened, then as the liquid level came even with the top of the resin bed a pulse of 20 milliliters of the aqueous feed mixture was introduced. As the liquid level drew even again with the top of the resin bed, 1-2 milliliters of DI water were added and the valve at the top of the column was closed. An elution flow of 20 milliliters per minute of DI water was begun, and 34 fractions of about 48 mL each were collected at 0.16 bed volume intervals for subsequent analysis.

Subsequently, 280 mL of Mitsubishi DIAION AMP-03 amphoteric ion exchange resin, described by Mitsubishi as an amphoteric ion exchange resin in which a quaternary ammonium group and a carboxyl group are incorporated on a cross-linked polystyrene frame, as having a uniform bead size of 260 μm and outstanding resistance to degradation and leaching, were slurried in DI water and loaded into two of the same jacketed glass columns in the same manner as for the weakly basic anion exchange resin Lewatit MDS 4368. A first column was conditioned/pretreated using the same aqueous feed mixture, while the second column was conditioned/pretreated with deionized water. Pretreatment was accomplished in a down flow configuration for the amphoteric resin columns, however, as no swelling was expected and none was in fact observed. After rinsing with deionized water as before, pulse testing was undertaken with the aqueous feed mixture in the same manner as with the MDS 4368 resin.

Analysis of the fractions collected from the elution of the MDS 4368 columns and of the AMP-03 columns, respectively, demonstrates by comparing the cumulative areas of overlap of the gluconic acid or glucaric acid fractions, as the case may be, with the fractions for all other materials on the one hand and for glucaric acid and gluconic acid specifically and respectively from among the "all other materials" on the other hand, that the amphoteric resin provided superior performance to the weakly basic anion exchange resin offered by Diamond et al., see Table 1 below. More particularly, the amphoteric resin proved a much more effective resin for isolating the glucaric acid from a product mixture of the type described in Boussie et al., as compared to the weakly basic anion exchange resin advocated by Diamond et al. In Table 1, "OAGnF" will be understood as referring to the overlapping area of the gluconic acid fraction with "all other materials" and with glucaric acid specifically from among the "all other materials", and "OAGrF" correspondingly will be understood as referring to the overlapping area of the glucaric acid fraction with "all other materials" and with gluconic acid specifically from among the "all other materials":

TABLE 1

Relative Areas of Overlap Between MDS 4368 and AMP-03 Pulse Tests

| | AMP-03 Resin Pulse Test Results | | MDS 4368 Resin Pulse Tests | |
|---|---|---|---|---|
| | Glucaric/ Others | Glucaric/ Gluconic | Glucaric/ Others | Glucaric/ Gluconic |
| OAGnF | 22.2 | 16.2 | 43.6 | 23.4 |
| OAGrF | 31.4 | 28.2 | 53.8 | 32.6 |

EXAMPLE 7

For this example, a glucarolactones feed was first generated by combining saccharic acid calcium salt (43.75 grams), acetone (148 mL) and deionized water (7 mL) in a 500 mL round bottom flask, to which 8.52 mL of concentrated sulfuric acid was added over the course of 30 minutes at room temperature. The mixture was then allowed to heat to reflux for 4 hours, and filtered to remove the calcium sulfate salts and washed with 150 mL acetone. Methyl isobutyl ketone was then added, and the flask contents rotovapped to remove solvent. $^1$H NMR indicated the formation of glucarolactones.

A portion (1.17 grams) of the glucarolactones thus formed was dissolved in 1.5 grams of deionized water and combined with 50 mL of n-butanol and 0.13 mL of concentrated sulfuric acid in the Dean-Stark equipped 3-neck round bottom flask arrangement used in Examples 1 and 2. The flask contents were then heated to 50 degrees Celsius at which time all of the lactones were fully dissolved. An acid alumina (0.19 grams of acid surface modified activated alumina from Dynamic Adsorbents, Inc., Norcross, Ga.) was added, and the mixture allowed to reflux over the course of 72 hours in an oil bath at 130 degrees Celsius, with samples pulled regularly for analyzing the progression of the esterification reaction and with continuous removal of water via the Dean-Stark trap. The final product (9.07 grams) was analyzed by gas chromatography and found to contain 3.34% by weight of dibutyl furan-2,5-dicarboxylate, for a molar yield of approximately 50% from the starting glucarolactones. Though a comprehensive quantitative analysis was not undertaken of the product mixture as a whole, a small amount of glucaromonolactones and unreacted glucarodilactones was observed to remain in the product mixture, while a comparatively larger amount of the dibutyl furan-2,5-dicarboxylate, furan-2,5-monobutylcarboxylic acid and furan-2,5-dicarboxylic acid were observed to be formed.

EXAMPLE 8

To evaluate the effect of carrying out the initial esterification step under pressure, 1.2 grams of a 48% mixture of glucaric and gluconic acids in water from Rennovia Inc, Santa Clara, Calif. (as such a mixture is described in U.S. Pat. No. 8,669,397 to Boussie et al) was combined with 40 mL of n-butanol and 0.13 mL of concentrated sulfuric acid, and this mixture was in turn placed in a 75 mL Parr multireactor. The vessel was sealed, purged three times with 3.4 MPa (500 psi) nitrogen and pressurized to 1.4 MPa, gauge (200 psig). A reaction temperature of 175 degrees Celsius was established and held for five hours with stirring at 800 rpm. Following analysis by $^1$H NMR, while an effort was again not undertaken to quantify the species identified, the final product was nevertheless found to contain more of the mono- and dilactones as compared to Example 7, and as to converted materials it appeared that more of the product was in the form of the monobutyl and dibutyl esters of FDCA as opposed to FDCA.

EXAMPLE 9

The same apparatus and procedure as used in Example 8 were employed to evaluate the effect of carrying out the esterification of 0.95 grams of a mixture of glucarodilactones as supplied by Rennovia Inc. under pressure. Nuclear magnetic resonance spectroscopy gave relatively similar results to the results described for Example 8.

Examples 10-17

A set of catalyst screening experiments were performed using a screening pressure reactor by Unchained Labs, to evaluate the effectiveness on the whole of various esterification catalysts for the first step of the process of the present invention as well as the extent to which the relative amounts of the 2,3- and 2,5-diesters could be influenced by the selection of a particular esterification catalyst (including the case where no extrinsic esterification catalyst was employed, and the esterification reaction was autocatalyzed).

For each screening experiment, glucarodilactones as employed in EXAMPLE 1 (200 mg), 1-pentanol (4 mL, Sigma-Aldrich, St. Louis Mo.) and, where applicable, 60 mg of catalyst (3.5 mL) were placed in 5 mL stainless steel reactor vials. The reactions were performed under 8.3 MPa (1200 psi) nitrogen and heated to 80 degrees Celsius for 2 hours. GC analysis provided the product compositions indicated in Table 2 below, where all numbers are expressed in terms of weight percent of the total product formed:

TABLE 2

| Catalyst | FDCA | 2,3-FDPE | 2,5-FDPE | 2-furoic acid | Ratio of 2,3:2,5[a] |
|---|---|---|---|---|---|
| None | 0 | 16 | 84 | 0 | 16:84 |
| Acidic alumina | 32 | 25 | 22 | 21 | 47:53 |
| Amberlyst ® 35 | 3 | 13 | 83 | 1 | 86:14 |
| Gallium triflate | 3 | 52 | 44 | 1 | 46:54 |
| Hafnium triflate | 3 | 52 | 44 | 1 | 46:54 |
| Acidic titania | 4 | 14 | 63 | 19 | 82:18 |
| Acidic carbon | 3 | 24 | 72 | 1 | 82:18 |
| TiO$_2$ | 29 | 15 | 5 | 50 | 75:25 |

[a]Expressed as percentages of the combined amounts by weight of the 2,3- and 2,5-diesters in the product mixture;

What is claimed is:

1. A process for making esters of 2,5-furandicarboxylic acid, comprising:
   reacting an aqueous feed comprising glucaric acid with a high boiling first alcohol in the presence of an acid catalyst and with removing water during the reaction, to form a first product mixture comprising a first ester of 2,5-furandicarboxylic acid and the high boiling first alcohol;
   removing unreacted high boiling first alcohol from the first product mixture;
   combining the first ester of 2,5-furandicarboxylic acid and the high boiling first alcohol with a lower boiling second alcohol selected from the group consisting of methanol, ethanol, isopropanol and n-propanol;

transesterifying the first ester with the lower boiling second alcohol to form a second product mixture comprising a second ester of 2,5-furandicarboxylic acid with the lower boiling second alcohol; and recovering the second ester of 2,5-furandicarboxylic acid with the lower boiling second alcohol.

2. The process of claim 1, wherein 2,3- and/or 2,5-isomers of the first diester
are present in the first product mixture and further comprising recovering at least a portion or portions of either or both of these isomers prior to the transesterification step.

3. The process of claim 2, wherein at least a portion of the 2,3-isomer is preferentially isolated from the first product mixture by distillation, solid-liquid extraction or chromatography.

4. The process of claim 1, wherein 2,3- and/or 2,5-isomers of the second diester are present in the second product mixture and further comprising separating the second product mixture into a first fraction enriched in the 2,3-isomer and a second fraction enriched in the 2,5-isomer by one or more of distillation, solid-liquid extraction, fractional crystallization and chromatography.

5. The process of any one of claims 1-4, wherein the high boiling first alcohol is
selected from the $C_4$ to $C_{11}$ linear alcohols and $C_4$ to $C_{11}$ branched alcohols.

6. The process of claim 5, wherein the high boiling first alcohol is selected from 2-ethyl-1-hexyl alcohol, isobutyl alcohol, 2-propylheptyl alcohol, isononyl alcohol, isodecyl alcohol, isooctyl alcohol, isoamyl alcohol, isohexyl alcohol, fusel oil and mixtures of any of these.

7. The process of claim 1, further comprising removing impurities
from the recovered second ester by one or more of distillation, crystallization, chromatography, absorption, adsorption and hydrotreating to reduce unsaturation.

8. The process of claim 7, further comprising adding an antioxidant or oxygen
scavenger to the recovered second ester.

9. The process of claim 8, further comprising storing or transporting the recovered second ester in or under a reduced oxygen environment.

10. The process of claim 1, wherein water is continuously removed from the
reaction to form the first ester.

11. The process of claim 1, wherein either or both of the formation of the first
ester and the transesterification of the first ester with the lower boiling second alcohol take place in a reduced oxygen environment.

12. The process of claim 1, further comprising recovering and recycling at least
a portion of high boiling first alcohol to the step of reacting the aqueous feed with high boiling first alcohol to form the first ester.

* * * * *